US005545158A

United States Patent [19]
Jessup

[11] Patent Number: 5,545,158
[45] Date of Patent: Aug. 13, 1996

[54] DISPOSABLE ABSORBENT GARMENT AND A CONTINUOUS, SELECTIVELY ELASTICIZED BAND JOINED THERE TO

[75] Inventor: James L. Jessup, Appleton, Wis.

[73] Assignee: Kimberly-Clark Corporation, Neenah, Wis.

[21] Appl. No.: 264,539

[22] Filed: Jun. 23, 1994

[51] Int. Cl.$^6$ .................................................. A61F 13/15
[52] U.S. Cl. ...................... 604/385.2; 604/393; 604/396; 604/373
[58] Field of Search .................................... 604/358, 373, 604/385.1–397; 2/401, 236, 237

[56] References Cited

U.S. PATENT DOCUMENTS

| | | |
|---|---|---|
| 1,544,312 | 6/1925 | Gray . |
| 2,976,199 | 3/1961 | Rand . |
| 3,604,015 | 9/1971 | Dove . |
| 3,687,141 | 9/1972 | Matsuda ................................. 604/397 |
| 3,966,527 | 6/1976 | Gros . |
| 4,033,801 | 7/1977 | Gros . |
| 4,450,026 | 5/1984 | Pieniak . |
| 4,486,192 | 12/1984 | Sigl . |
| 4,525,407 | 6/1985 | Ness . |
| 4,543,154 | 9/1985 | Reiter . |
| 4,563,185 | 1/1986 | Reiter . |
| 4,641,381 | 2/1987 | Heran et al. . |
| 4,652,487 | 3/1987 | Morman . |
| 4,657,802 | 4/1987 | Morman . |
| 4,663,220 | 5/1987 | Wisneski et al. . |
| 4,720,415 | 1/1988 | Vander Wielen et al. . |
| 4,808,252 | 2/1989 | Lash . |
| 4,861,652 | 8/1989 | Lippert et al. . |
| 4,883,549 | 11/1989 | Frost et al. . |
| 4,916,005 | 4/1990 | Lippert et al. . |
| 4,925,520 | 5/1990 | Beaudoin et al. . |
| 4,940,464 | 7/1990 | Van Gompel et al. . |

FOREIGN PATENT DOCUMENTS

| | | |
|---|---|---|
| 0217032 | 4/1987 | European Pat. Off. . |
| 0526868 | 2/1993 | European Pat. Off. . |
| 0547497 | 6/1993 | European Pat. Off. . |
| 0919292 | 2/1963 | United Kingdom . |
| 2257347 | 1/1993 | United Kingdom . |
| WO9325171 | 12/1993 | WIPO . |
| WO9409736 | 5/1994 | WIPO . |

*Primary Examiner*—Robert A. H. Clarke
*Attorney, Agent, or Firm*—Douglas L. Miller

[57] ABSTRACT

A disposable absorbent garment comprises a pair of elastic side sections, front and back sections, and a continuous, selectively elasticized waistband operatively joined thereto. The waistband does not substantially inhibit the elasticity of the elastic side sections, and provides the same or different elasticity to the front and back sections.

18 Claims, 7 Drawing Sheets

5,545,158

DISPOSABLE ABSORBENT GARMENT AND A CONTINUOUS, SELECTIVELY ELASTICIZED BAND JOINED THERE TO

BACKGROUND OF THE INVENTION

The present invention relates to disposable absorbent garments, and more particularly to a disposable absorbent garment and a continuous, selectively elasticized band joined about an opening thereof for improving fit and comfort.

In the last several years, disposable absorbent garments have become available for use by children in the potty-training stage, and have proved to be extremely popular with mothers and caretakers. A specific example is a training pant comprising a bodyside liner, an outer cover, an absorbent medium between the liner and the outer cover, and side seams that bond portions of the side edges of the pant together to form waist and leg openings.

One style of training pant has elastic side panels that fit against the hips of the child, and discrete front and back elastic waist strips adjacent the waist opening. The waist strips generally are spaced from the elastic side panels.

Although these discrete front and back elastic waist strips may provide some gasketing at the front and back of the pant, they are not entirely effective in providing the desired gasketing and fit at the waist resulting in satisfactory waste containment.

SUMMARY OF THE INVENTION

In one form of the invention there is provided a disposable garment comprising a pant body defining a waist opening and a pair of leg openings; a partially elastic, continuous waistborder comprising a pair of elastic side segments and at least one non-elastic segment; and a continuous, elastic waistband joined to the partially elastic, continuous waistborder.

In another form of the present invention there is provided a disposable garment comprising a pant body having a continuous waistborder defining a continuous waist opening, and in which the continuous waistborder has at least one non-elastic segment and at least one elastic segment; and a continuous elastic waistband comprising at least one recoverable portion that is capable of being temporarily inhibited, and at least one elastic portion having an elasticity substantially the same as an elasticity of the elastic segment. The continuous waistband is joined to the continuous waistborder with the elastic portion joined to the elastic segment, and the recoverable portion joined to the non-elastic segment. The recoverable portion, upon being activated, gathers the non-elastic segment.

In still another form of the present invention there is provided a disposable absorbent garment comprising a topsheet, a backsheet including a waistborder having at least one elastic segment and a non-elastic segment, and an absorbent structure disposed on the backsheet. An elastic waistband is joined to the waistborder and has an elasticity substantially the same as an elasticity of the elastic segment.

BRIEF DESCRIPTION OF THE DRAWINGS

The above-mentioned and other features of the present invention and the manner of attaining them will become more apparent, and the invention itself will be better understood by reference to the following description of the invention, taken in conjunction with the accompanying drawings, wherein.

DEFINITIONS

Figure 1:
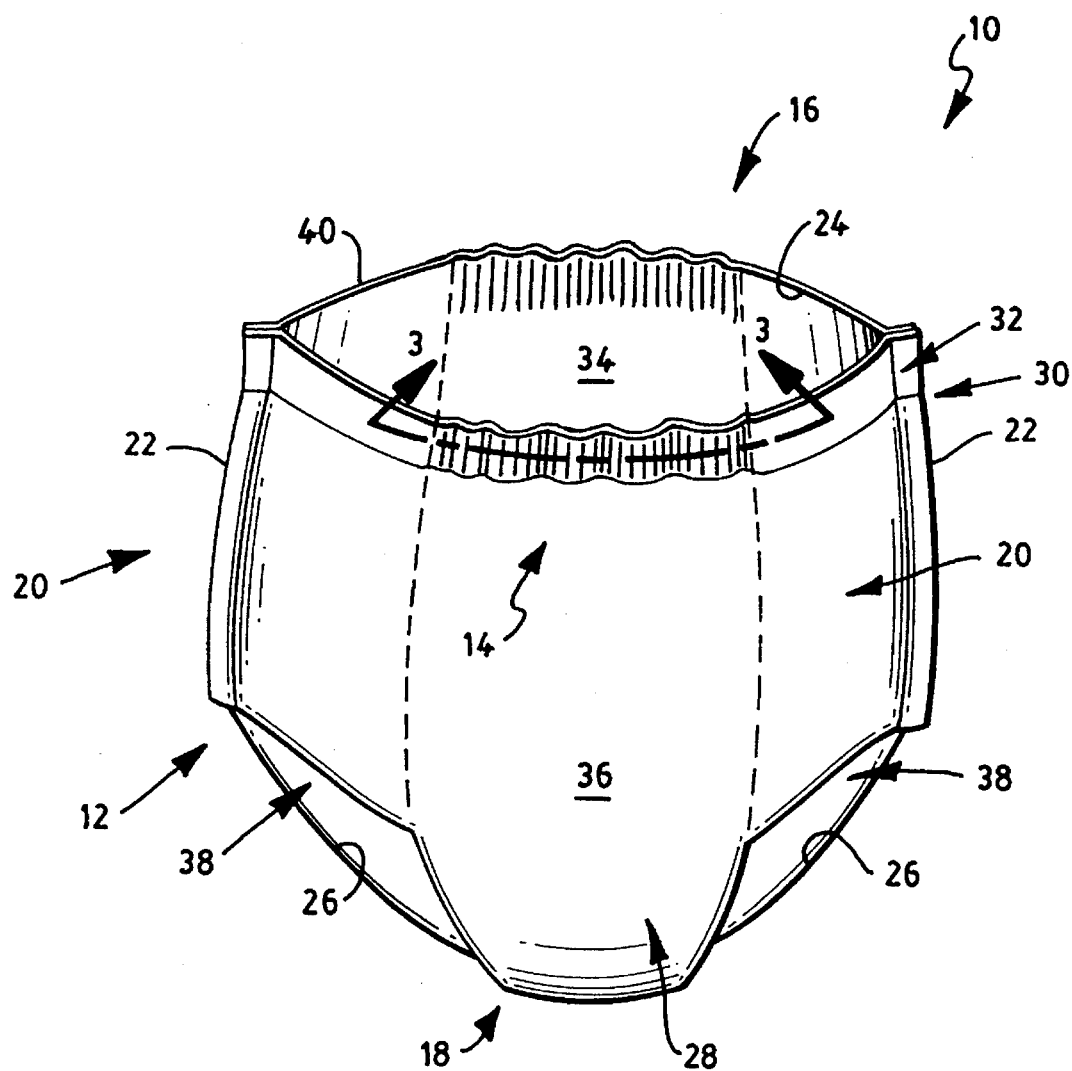
FIG. 1 illustrates a front perspective view of one type of a disposable elasticized, absorbent garment incorporating the principles of the present invention.

Each of the following terms used herein include the following meaning:

"Composite elastic material" or "composite elastic web" means a multi-layered material having at least one elastic layer joined to at least one gatherable layer at least at two locations wherein the gatherable layer is gathered between the locations where it is joined to the elastic layer. A composite elastic material may be stretched to the extent that the non-elastic material gathered between the bond locations allows the elastic material to extend. This type of composite elastic material is disclosed, for example, by Vander Wielen et al., U.S. Pat. No. 4,720,415 issued Jan. 19, 1988, the content of which is incorporated by reference herein.

"Continuous" means that the described structure is a closed-loop structure. The continuous structure may be unitary, i.e., a one-piece structure, or may be made up of individual elements suitably joined together to form a closed-loop.

"Disposable" means that the described garment is designed to be used until soiled, either by urination, defecation, or otherwise, and then discarded, rather than being washed and used again.

"Elastic", "elasticity", "elasticized", or the like, refers to a material or composite material that tends to recover its original size and shape after removal of the force causing the deformation (expressed in %).

"Elongation" means the ratio of the extension of a material to the length of the material prior to the extension (expressed in percent), as represented by the following:

$$\frac{\text{extended length} - \text{original length}}{\text{original length}} \times 100.$$

"Extension" means the change in length of a material due to stretching (expressed in units of length).

"Join", "joining", "joined", or variations thereof, when used in describing the relationship between two or more elements, means that the elements can be connected together in any suitable manner, such as by heat sealing, ultrasonic bonding, thermal bonding, by adhesives, stitching, or the like. Further, the elements can be joined directly together, or may have one or more elements interposed between them, all of which are connected together.

"Operatively elastically joined" describes the joining of an elastic member to a non-elastic member such that the two joined members exhibit elasticity.

"Pant body" refers to a garment that has a waist opening and a pair of leg openings, similar to shorts, swim wear, or the like. The described garment may or may not have a manually tearable side seam.

"Recover", "recovering", or variations thereof, refers to a contraction of an extended material upon termination or removal of a biasing force, or upon suitably treating the material after it has been temporarily inhibited.

"Temporarily inhibit" means to delay the total recovery of an extended elastic layer (or substrate) or composite elastic material. The delay may be imparted by compressing the extended elastic layer, or by compressing the composite elastic material so that the elastic and gatherable layers are temporarily joined. Partial recovery of a temporarily inhibited elastic layer or composite elastic material may occur immediately after the force is removed, but total recovery of such a temporarily inhibited elastic layer or composite elastic material will require more time than the total recovery of the same material which has not been temporarily inhibited. For example, total recovery of an extended elastic layer or composite elastic material that has not been temporarily inhibited may be instantaneous, whereas the total recovery of a temporarily inhibited elastic layer or composite elastic material may take, for example, from about 5 to about 60 seconds.

"Total recovery", or variations thereof, refers to a material recovering to generally within about 20 percent of its relaxed, preextended dimension.

DETAILED DESCRIPTION

Referring primarily to FIG. 1, there is illustrated disposable absorbent garment 10 in the form of a child's training pant. Although garment 10 is illustrated and will be described as a training pant, it can be other types of absorbent garments or articles, such as baby diapers, adult incontinence products, or the like.

Figure 2:
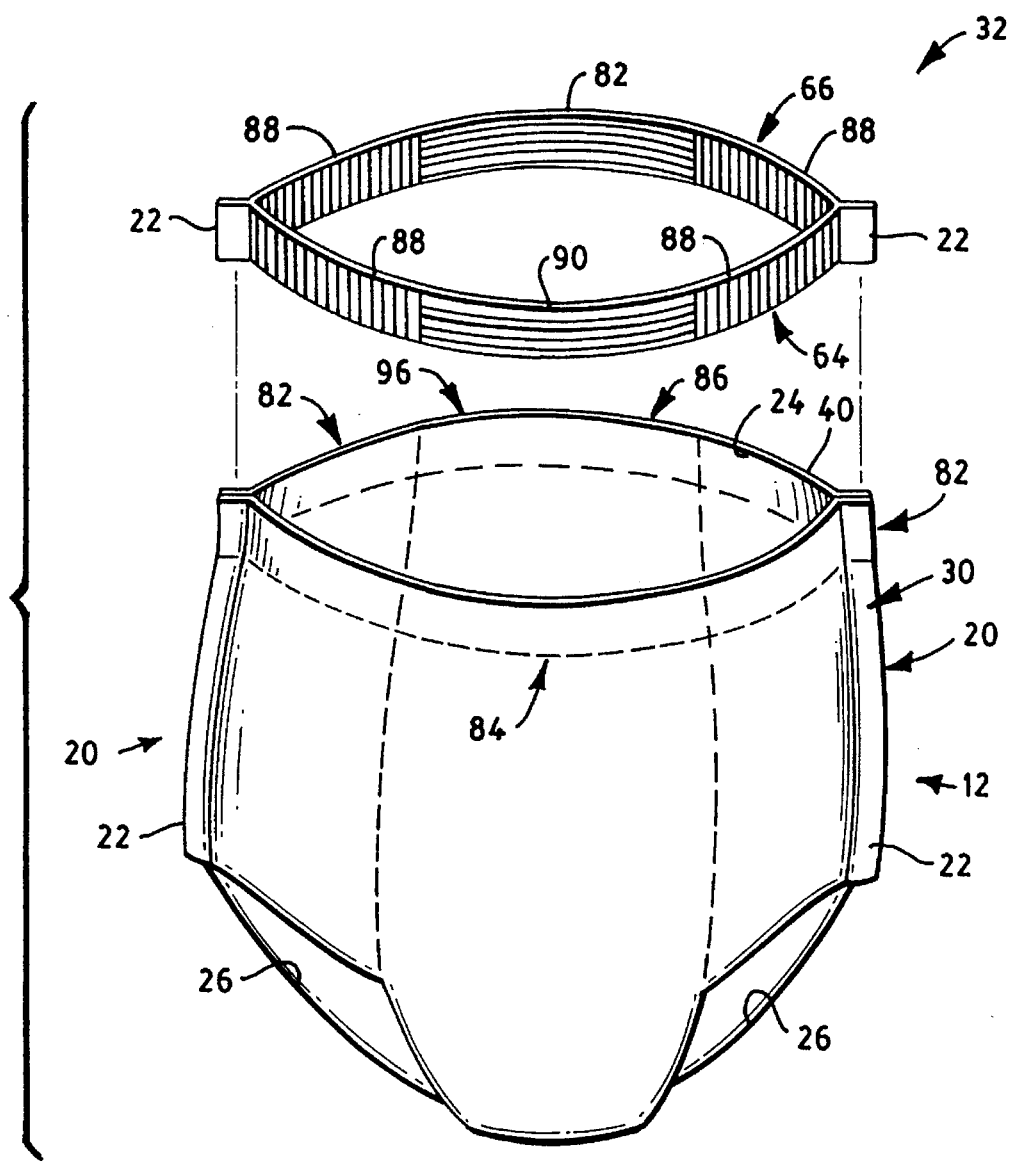
FIG. 2 illustrates a partially exploded view of FIG. 1 with a continuous, selectively elasticized waistband separated from the garment.
Figure 3:
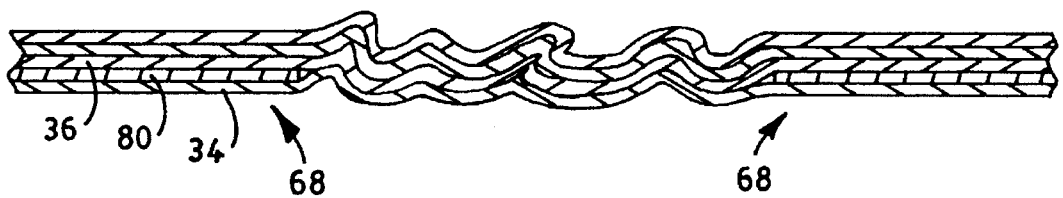
FIG. 3 illustrates a cross-sectional view of FIG. 1 taken along line 3—3 and viewed in the direction of the arrows.

Disposable absorbent garment 10 includes a pant body 12 comprising a front section 14, a back section 16, a crotch section 18, elastic side sections 20, seams 22, a continuous waist opening 24, and a pair of continuous leg openings 26. Each elastic side section 20 includes a front elastic side member 68 (FIG. 5) and a back elastic side member 70, which are joined together at a respective seam 22. Garment 10 further includes a continuous waistborder 30 (FIGS. 1 and 2), continuous legborders 38, and a continuous waistband 32. Continuous waistband 32 comprises front waistband member 64 (FIG. 5) and back waistband member 66. Continuous waistborder 30 comprises front waistborder section 42 (FIGS. 4, 5) having front edge 44 and back waistborder section 46 having back edge 48. An absorbent structure 28 is suitably incorporated in garment 10 at least at crotch section 18 thereof.

Pant body 12 includes a topsheet 34 (FIG. 4) and a backsheet 36, which are desirably coincident with one another, although not a requirement of the present invention. Backsheet 36 (FIG. 5) includes a pair of front outer edges 50, front inner edges 52, innermost edges 54, back sloping edges 56, and back outer edges 58.

Front waistband member 64 (FIGS. 4, 5) is suitably joined to front waistborder section 42, and back waistband member 66 is suitably joined to back waistborder section 46. Front and back waistborder sections 42, 46 desirably have respective lengths substantially corresponding to the respective lengths of front and back waistband members 64, 66, and widths substantially corresponding to the respective widths of front and back waistband members 64, 66; length being measured along a line generally parallel to transverse centerline 60 (FIG. 5) and width being measured along a line generally parallel to longitudinal centerline 62. A desired width range of waistband members 64, 66 is between about 1 centimeter to about 8 centimeters, and a more desired range is between about 2 centimeters to about 4 centimeters. In the case where, for example, one or both of the waistband members 64, 66 have some other geometric shape, i.e., not an elongate rectangular shape as illustrated in FIGS. 4 and 5, each waistborder section 42, 46 desirably would have substantially the same geometric shape as its respective waistband member 64, 66.

Figure 5:
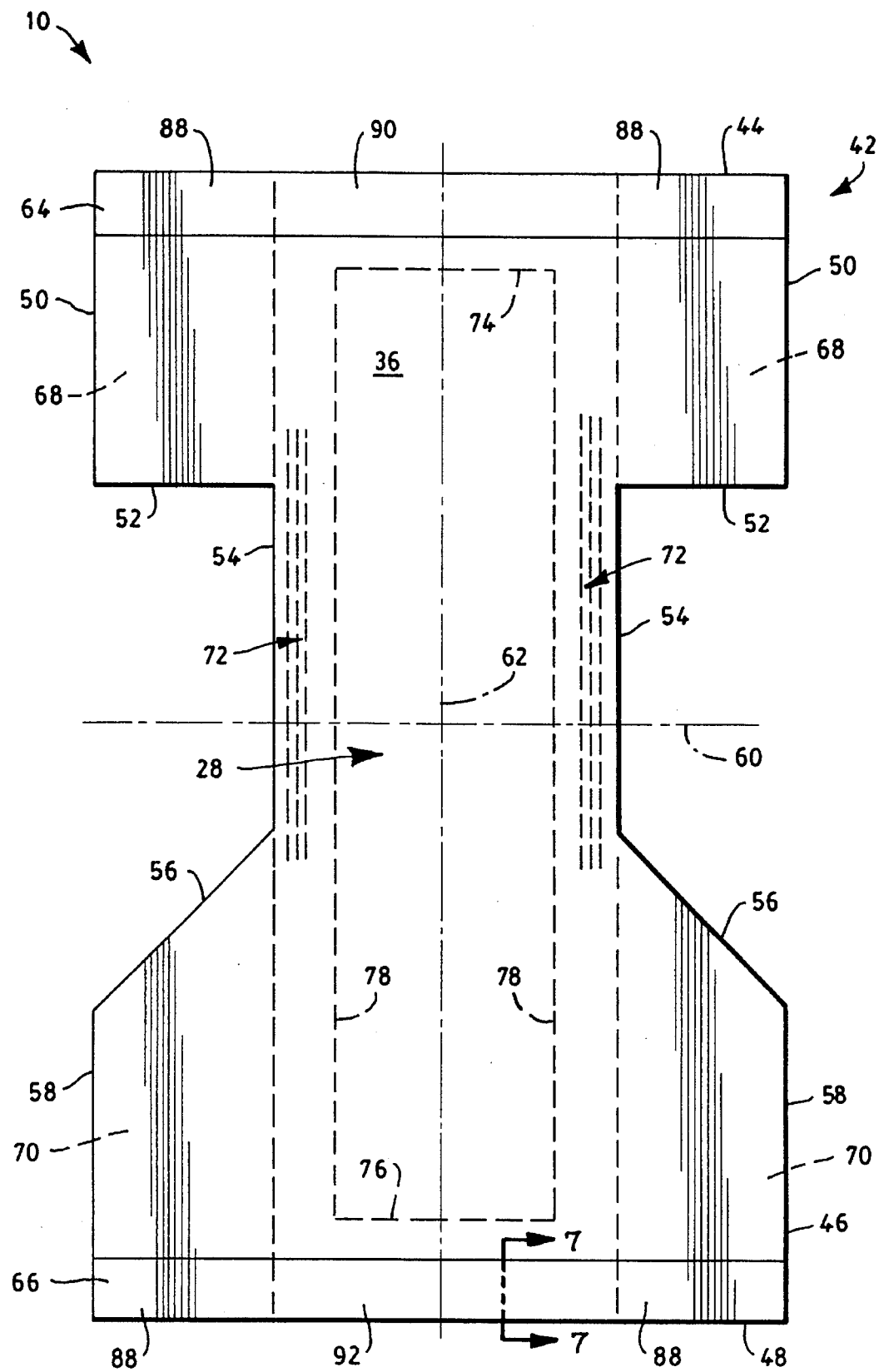
FIG. 5 illustrates a top plan view of the garment in FIG. 1 in a partially disassembled, extended flat state.

With reference primarily to FIGS. 1 and 5, when garment 10 is folded along a transverse fold-line, which is generally parallel to transverse centerline 60, and pairs of aligned front and back outer edges 50, 58 are joined together to form seams 22, the following construction is accomplished: (i) front waistborder section 42 and back waistborder section 46 form or define continuous waistborder 30; (ii) front waistband member 64 and back waistband member 66 form or define continuous waistband 32; (iii) a front inner edge 52, an innermost edge 54, and a back sloping edge 56 form or define a respective leg opening 26; (iv) and a front elastic side member 68 and a back elastic side member 70 form or define a respective elastic side section 20.

Figure 4:
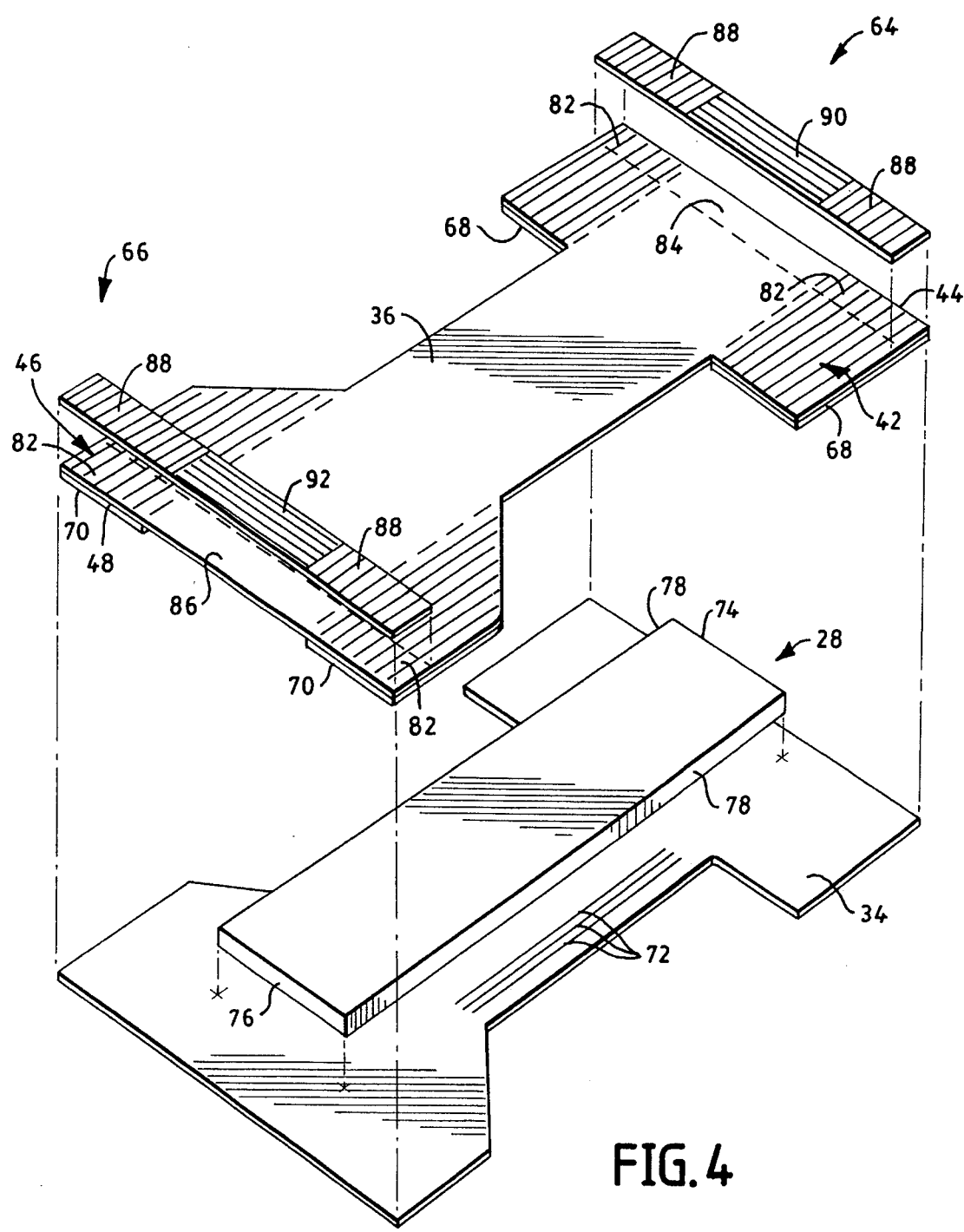
FIG. 4 illustrates an exploded, perspective view of the garment in FIG. 1 in a partially disassembled, extended flat state.

Garment 10 also comprises a pair of leg elastic members 72 (FIG. 5) that are suitably joined, for example, between topsheet 34 and backsheet 36 (FIG. 4).

Absorbent structure 28 (FIGS. 4 and 5) comprises front absorbent edge 74, back absorbent edge 76, and absorbent side edges 78. As illustrated in FIG. 5, front absorbent edge 74 and back absorbent edge 76 are respectively inboard of front waistband member 64 and back waistband member 66. Similarly, absorbent side edges 78 are inboard of respective leg elastic members 72. By "inboard" is meant that absorbent front edge 74, for example, is closer to transverse centerline 60 than front waistband member 64, and absorbent side edges 78 are closer to longitudinal centerline 62 than leg elastic members 72.

When garment 10 is properly fitted on the wearer, topsheet 34 faces toward the body of the wearer, and may or may not be the layer that directly contacts the skin. Topsheet 34 can be a liquid permeable, elastic or non-elastic, substantially hydrophobic material, such as a spunbonded web of synthetic polymer filaments. Topsheet 34 can also be a meltblown web or a bonded carded web of synthetic polymer filaments. Suitable synthetic polymers include, for example, polyethylene, polypropylene, and polyesters. Topsheet 34 has a pore size that readily allows the passage therethrough of liquids, such as urine and other body exudates. If desired, topsheet 34 can be treated with surfactants to selectively adjust its degree of wettability, and can also be selectively embossed or perforated with discrete slits or holes extending therethrough. Suitable topsheet materials can have a basis weight between about 10 grams per square meter (gsm) to about 26 gsm, and a thickness between about 0.013 centimeters to about 0.064 centimeters. The thickness of the topsheet material can be determined by employing an Ames Bulk Test (ASTM D-1777) performed at a restraining pressure of 0.2 psi (1.38 kPa).

Backsheet 36, which may or may not be the outermost layer of garment 10, can be liquid permeable or liquid impermeable, and may or may not have breathability, i.e., be vapor permeable. A suitable liquid permeable backsheet 36 is a nonwoven bicomponent web having a basis weight between about 15 gsm to about 50 gsm. The nonwoven bicomponent web may be a spunbond bicomponent web, or a bonded carded bicomponent web. Suitable bicomponent fibers are a wettable, polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multilobe, side-by-side or end-to-end. Another suitable liquid permeable material is a liquid permeable spunbond polypropylene nonwoven web having a basis weight between about 15 gsm to about 50 gsm.

A suitable liquid impermeable backsheet 36 is a 0.0015 centimeter polyethylene film from Edison Plastics Company, South Plainfield, New Jersey. Backsheet 36 can also be a two-ply laminate, in which the innermost layer can be the above-described liquid impermeable film or any other suitable liquid impermeable layer, and the outermost layer can be the above-described liquid permeable spunbond polypropylene nonwoven web or any other suitable liquid permeable layer. Backsheet 36 desirably has a thickness within the range of about 0.0013 to about 0.0051 centimeters.

Absorbent structure 28 can comprise any suitable absorbent material, natural or synthetic, or a combination thereof, along with superabsorbent material. The absorbent material of which absorbent structure 28 is made may also be encased in a tissue wrap (not shown) in order to maintain the integrity of the absorbent material comprising absorbent structure 28. Suitable superabsorbent materials are available from various vendors, such as Dow Chemical Company, Hoechst-Celanese Corporation, and Allied Colloids, Inc. A suitable natural absorbent material is a wood pulp fluff identified by the trade designation CR1654 from Kimberly-Clark Corporation, Neenah, Wis. One specific absorbent structure 28 that can be suitably used in garment 10 is described in U.S. patent application Ser. No. 08/096,654 filed Jul. 22, 1993, inventors Hanson et al., which is assigned to the assignee of this application, the content of which is incorporated by reference herein.

The construction of garment 10 can be accomplished in any conventional manner well known in the art. For example, the structural elements can be joined together in any manner, such as by heat sealing or ultrasonic bonding, or by adhering the elements together with a suitable adhesive. Suitable adhesives can be obtained from Findley Adhesives, Inc., Wauwatosa, Wis., and can be applied in any manner, such as by spraying, slot-coat extrusion, printing, or the like. The applied adhesive can be in any desired configuration, such as continuous or discontinuous beads, continuous or discontinuous swirls, meltblown patterns, spray patterns, or the like.

Referring to FIGS. 1–6, front elastic side members 68 (FIG. 5) can have the same or different geometry from back elastic side members 70. Each front elastic side member 68 and each back elastic side member 70 comprises an elastic layer 80 (FIG. 3, 6) sandwiched between topsheet 34 and backsheet 36. Elastic layer 80 can be any suitable elastic material, one such material being a block copolymer of styrene-ethylbutadiene-styrene. Other types of materials of which elastic layer 80 can be made are the KRATON® G series from The Shell Chemical Company such as KRATON® G-1650, KRATON® G-1652, KRATON® GX-1657 and KRATON® G-2740X. The KRATON® D series can also be used, as well as polyester elastomeric materials, polyurethane elastomeric materials, and polyamide elastomeric materials. Elastic layer 80 can be a film, nonwoven web, or ribbons or threads of synthetic or natural rubber arranged, for example, in a spaced, parallel manner.

Each elastic layer 80 is operatively elastically joined to a portion of either topsheet 34 or backsheet 36, preferably to portions of both topsheet 34 and backsheet 36, in order to provide elasticity to those portions. One example of this is disclosed in U.S. patent application Ser. No. 08/461,947 filed Jun.5, 1995, inventor Van Gompel et al., which s incorporated by reference herein. Another example of providing elastic side sections 20 is described in U.S. Pat. No. 4,940,464, issued Jul. 10, 1990, to inventor Van Gompel et al., which is incorporated by reference herein.

Still other examples of elastic materials and composites are described in U.S. Pat. No. 4,720,415, issued Jan. 19, 1988, to Vander Wielen et al.; U.S. Pat. No. 4,657,802, issued Apr. 14, 1987, to Morman; and U.S. Pat. No. 4,652, 487 issued Mar. 24, 1987, to Morman; the contents of these three patents being incorporated by reference herein.

Each elastic side section 20 in disposable absorbent garment 10 (FIG. 1) can have an elasticity between about 50% to about 250%, desirably an elasticity between about 75% to about 200%, and more desirably an elasticity between about 100% to about 150%.

Figure 6:
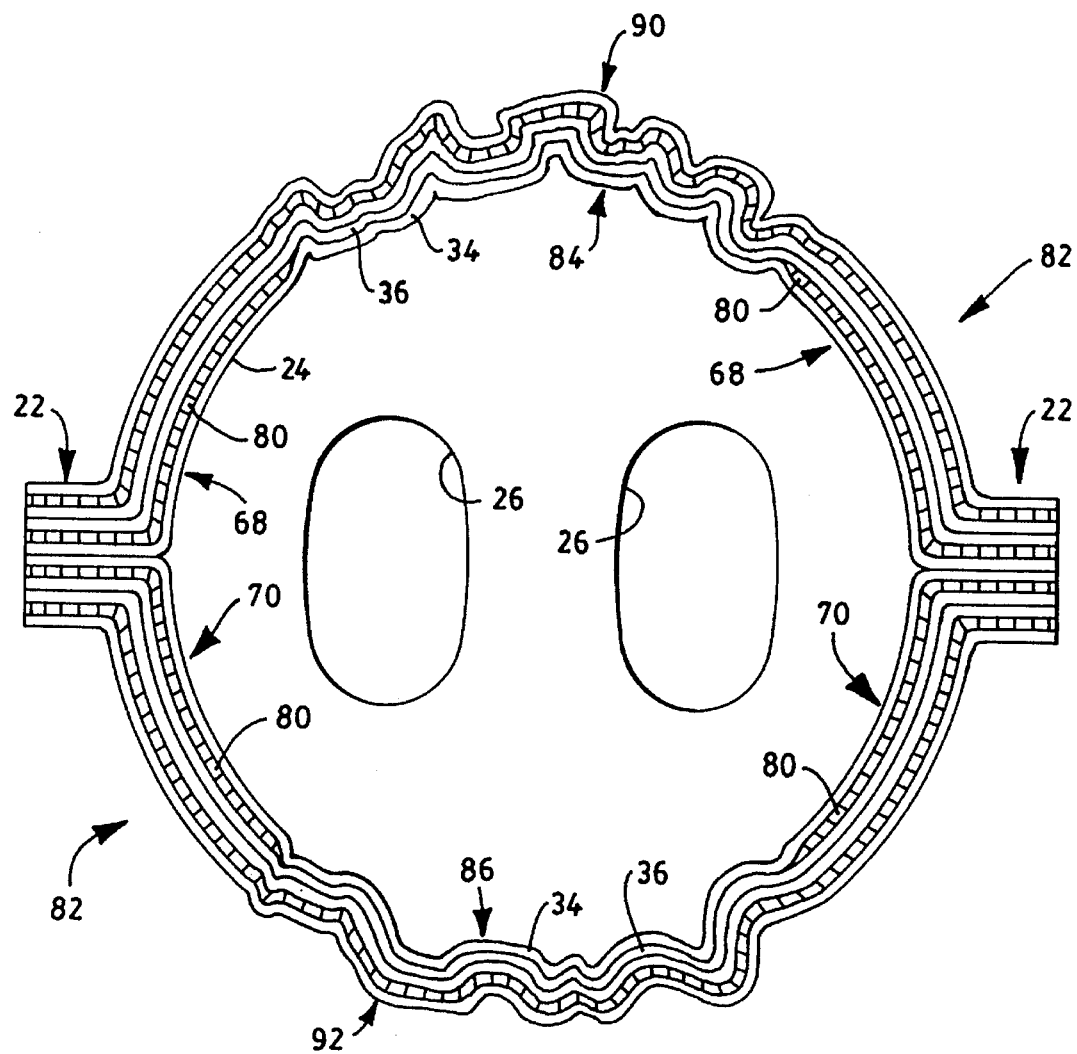
FIG. 6 illustrates a top plan view of the garment in FIG. 1.

Referring primarily to FIGS. 2, 4–6, continuous waistborder 30 (FIG. 2) comprises oppositely disposed elastic side segments 82, non-elastic front segment 84, and non-elastic back segment 86. Each elastic side segment 82 includes a portion of a respective elastic side section 20. Non-elastic front segment 84 and non-elastic back segment 86, as illustrated in FIG. 6, include portions of topsheet 34 and backsheet 36. Thus, continuous waistborder 30 (FIG. 2) is partially elastic due to elastic side segments 82.

Continuous waistband 32 can be an elastomeric, cloth-like, nonwoven fibrous material, such as an elastomeric stretch bonded laminate web or an elastomeric meltblown web. By proper selection of materials, continuous waistband 32 can be rendered temporarily elastically inhibited, such as by compression. Once temporarily elastically inhibited, the elastic material, of which waistband 32 is comprised, can be activated, such as by treating with heat, to recover to a state of elasticity.

In one specific embodiment, waistband 32 comprises an elastomeric nonwoven fibrous web that is substantially vapor-permeable. Examples of suitable elastomeric nonwoven fibrous webs are described in U.S. Pat. No. 4,663,220 issued May 5, 1987, to Wisneski et al., which is incorporated by reference herein. Examples of composite fabrics comprising at least one layer of nonwoven textile fabric joined to a fibrous elastic layer are described in European Patent Application EPA 0 217 032 published on Apr. 8, 1987, inventors J. Taylor et al., which is incorporated by reference herein. The composite nonwoven fabrics are commonly referred to as stretch bonded laminates.

In another embodiment, waistband 32 comprises a composite elastomeric web comprising individual, discrete strips or strands of elastomeric material secured to one or more nonwoven fibrous layers. Such a composite elastomeric web may, for example, comprise an elastomeric meltblown material arranged in a selected pattern of strips and suitably sandwiched and joined between two layers of nonwoven fibrous material. This material, as well as others, is described in U.S. Pat. No. 4,861,652 issued Aug. 29, 1989, the content of which is incorporated by reference herein. Still other useful composite elastic materials are described in U.S. Pat. No. 4,883,549, issued Nov. 28, 1989, which is incorporated by reference herein.

One of the innovative features of the present invention is selectively providing portions of continuous waistband 32 (FIGS. 1–2) with different elasticities as determined by, for example, the elasticity of elastic side sections 20 and the desired elasticity to be provided to non-elastic front segment 84 and/or non-elastic back segment 86.

Another novel feature of the present invention is providing a continuous waistband 32 about a continuous waistborder 30 such that it does not substantially restrict or diminish the elasticity of elastic side sections 20, and can provide a desired elasticity to non-elastic front and back segments 84, 86.

Following is one example of a selectively elasticized continuous waistborder 30. With reference to FIGS. 4 and 5, front and back waistborder sections 42, 46 define continuous waistborder 30 (FIG. 1), and have front and back waistband members 64, 66 suitably joined thereto, respectively. Since the joining of front waistband member 64 to front waistborder section 42 can be identical to the joining of back waistband member 66 to back waistborder section 46, a description only of the former will be given. In this example, each elastic side segment 82 (FIG. 2) has an elasticity of about 180%, i.e., each elastic side segment 82 can be extended 2.8 times its original length. It is desired that non-elastic front segment 84 be given an elasticity different from that of elastic side segment 82.

Front waistband member 64 (FIGS. 4, 5) includes side portions 88 and a recoverable front portion 90 therebetween. It is desired that front waistband member 64 be a unitary structure. However, side portions 88 and front portion 90 can be separate structures suitably joined together to form front waistband member 64. Since elastic side segments 82 (FIG. 2) have an elasticity of about 180%, front waistband member 64 is selected and configured also to have an elasticity of about 180%. Each side portion 88 in FIG. 4 has a length, as measured along centerline 60 (FIG. 5), of about 50 millimeters, and recoverable front portion 90 has a length of about 90 millimeters.

Front waistborder section 42 in FIG. 4 includes two elastic side segments 82 sandwiching non-elastic front segment 84. Each side segment 82 in FIG. 4 has a length of about 50 millimeters, and front segment 84 has a length of about 150 millimeters. Prior to joining front waistband member 64 to front waistborder section 42, recoverable front portion 90 is elongated about 67%, which results in an extended length of about 150 millimeters. After extending recoverable front portion 90, it is temporarily elastically inhibited such as by, for example, compression, thereby providing front portion 90 with the property of being totally recoverable, i.e., able to return to an elastic condition upon being suitably activated, such as by treating with heat. After front portion 90 has been extended and temporarily elastically inhibited, front waistband member 64 is suitably intermittently joined, such as by ultrasonic, heat, or adhesive point bonding, to front waistborder section 42, such that front portion 90 is joined to front segment 84.

In a similar manner, back waistband member 66 is joined to back waistborder section 46. Thereafter, disposable absorbent garment 10 is folded along a fold line generally parallel to transverse centerline 60, and front outer edges 50 (FIG. 5) are suitably bonded to back outer edges 58 to form seams 22. Garment 10 is then treated, such as with heat, in order to activate temporarily elastically inhibited front portion 90 and back portion 92. Upon total recovery, front portion 90 will gather non-elastic front segment 84 and back portion 92 will gather non-elastic back segment 86. Depending upon the selection of materials for front and back waistborder sections 42, 46 and front and back waistband members 64, 66, front segment 84 and front portion 90, when joined together, can have an elasticity between about 30% to about 60%.

It will be appreciated that the elasticity about waist opening 24 of garment 10 (FIG. 1) depends on various factors, such as the types of materials of which waistband 32 and waistborder 30 are comprised, their elastic characteristics, and the like. Thus, continuous waistband 32 will need to be carefully designed and constructed, as to materials and elasticity, so that once it is suitably joined to continuous waistborder 30, front and back segments 84, 86 will be given the desired elasticity.

Figure 7:
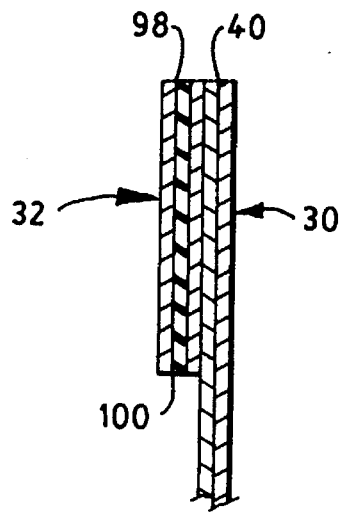
FIG. 7 illustrates a cross-sectional view through a waist portion of the garment in FIG. 1.

Continuous waistband 32 can be suitably joined to continuous waistborder 30 in a number of desired configurations. FIG. 7 illustrates one configuration in which continuous waistband 32 and continuous waistborder 30 are joined together such that top edge 98 of continuous waistband 32 is substantially coplanar with peripheral edge 40 of continuous waistborder 30.

Figure 7A:
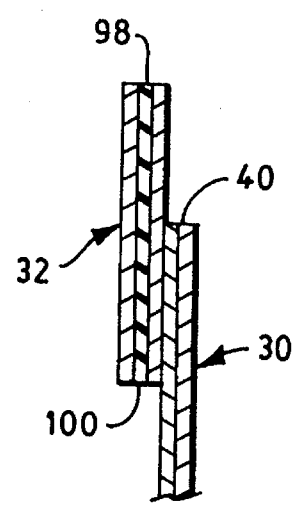
FIG. 7A illustrates a modification of the view in FIG. 7.

FIG. 7A is similar to FIG. 7 except that continuous waistband 32 is offset from continuous waistborder 30, such that a portion of waistband 32 extends beyond continuous waistborder 30. In this configuration, top edge 98 extends beyond peripheral edge 40.

Figure 7B:
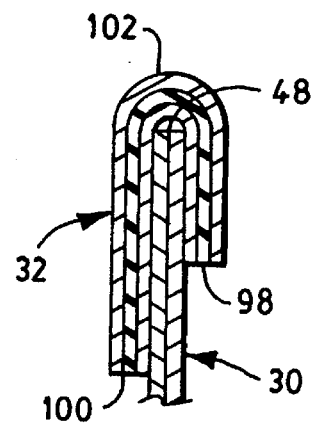
FIG. 7B illustrates a second modification of the view in FIG. 7.

Referring to FIG. 7B, continuous waistband 32 has a folded portion 102 that is folded over peripheral edge 40, such that top edge 98 is on the side of continuous waistborder 30 opposite from bottom edge 100.

Figure 7C:
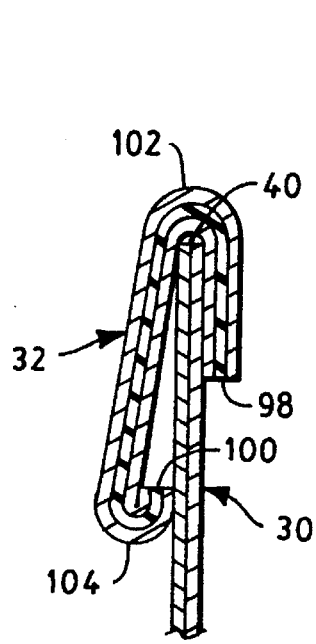
FIG. 7C illustrates a third modification of the view in FIG. 7.

The configuration in FIG. 7C is similar to that in 7B, except that the portion of continuous waistband 32 comprising bottom edge 100 has been folded upon itself to create a C-fold portion 104.

Figure 7D:
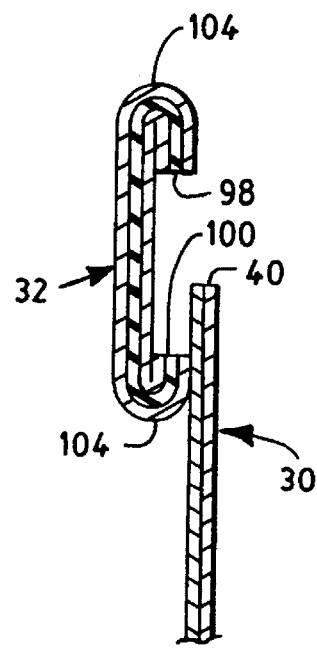
FIG. 7D illustrates a fourth modification of the view in FIG. 7.

The configuration in FIG. 7D illustrates continuous waistband 32 having two C-fold portions 104, with the C-fold portion 104 that includes bottom edge 100 being suitably joined to continuous waistborder 30. In this configuration, top edge 98 extends beyond peripheral edge 40.

Figure 8:
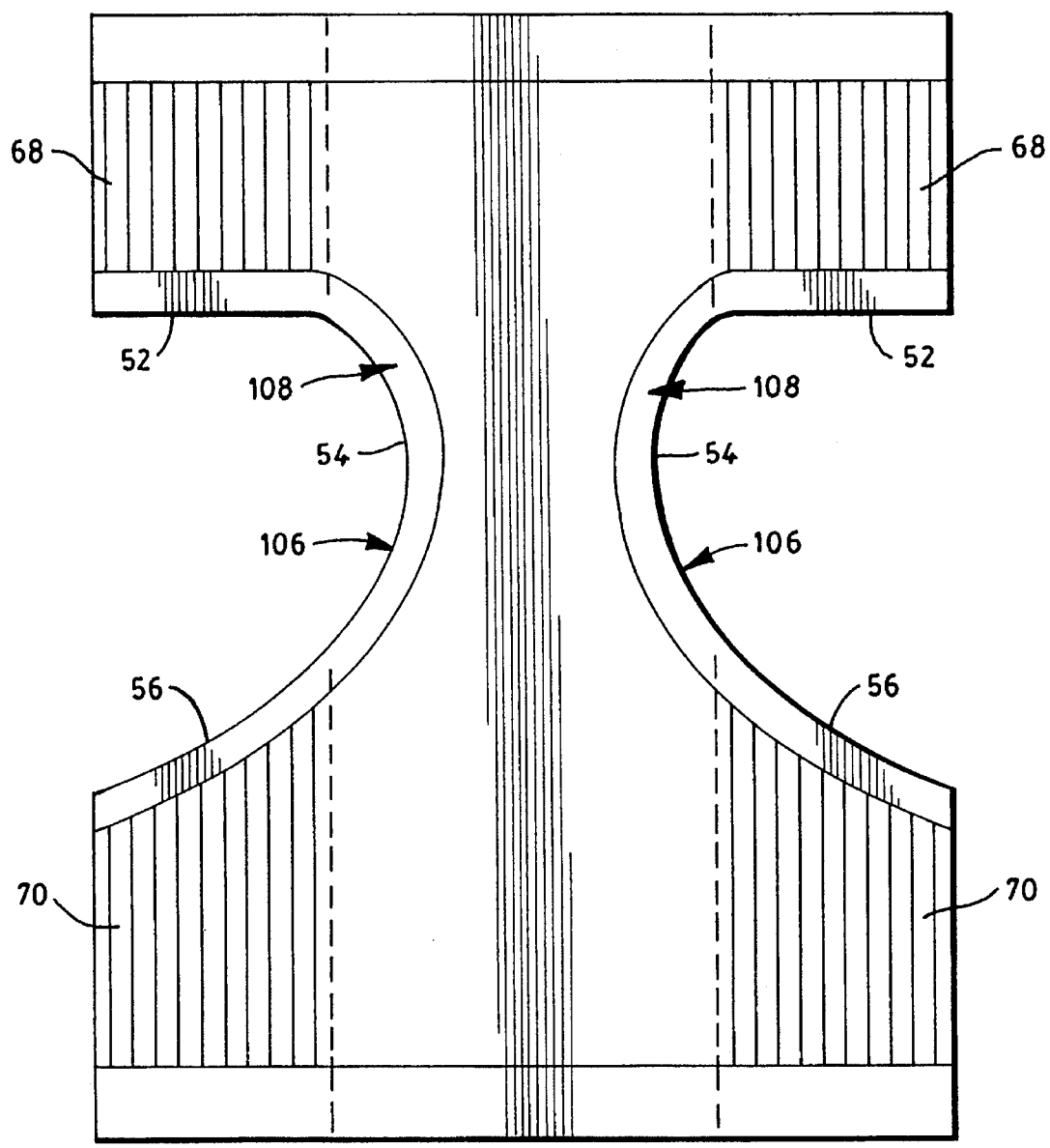
FIG. 8 illustrates a modification of the garment in FIG. 5.

FIG. 8 illustrates a modification to disposable absorbent garment 10 illustrated in FIG. 1, in which elastic legbands 106 have replaced leg elastic members 72 and have been suitably joined to legborders 108. An elastic legband 106 can be suitably joined to a legborder 108 in a manner similar to the joining of front waistband member 64 to front waistborder section 42 (FIG. 5).

While this invention has been described as having a preferred embodiment, it will be understood that it is capable of further modifications. This application is therefore intended to cover any variations, equivalents, uses, or adaptations of the invention following the general principles thereof, and including such departures from the present disclosure as come or may come within known or customary practice in the art to which this invention pertains and falls within the limits of the appended claims.

What is claimed is:

1. A disposable garment, comprising:

a pant body defining a waist opening and a pair of leg openings, a partially elastic, continuous waistborder comprising a pair of elastic side segments and at least one non-elastic segment, and a continuous, elastic waistband joined to said partially elastic, continuous waistborder; said waistband comprising a pair of side portions, a front portion, and a back portion, said pair of side portions being respectively joined to said pair of elastic side segments of said waistborder, one of said front portion and said back portion being operatively elastically joined to said non-elastic segment, said one portion and said non-elastic segment having an elasticity different from the elasticity of said elastic side segments.

2. The garment claim 1 wherein said waistband has a width between about 1 centimeter to about 8 centimeters.

3. The garment of claim 2 wherein said waistband is folded over a peripheral edge of said waistborder.

4. The garment of claim 2 wherein said waistband is C-folded upon itself.

5. The garment of claim 2 wherein said waistband extends beyond a peripheral edge of said waistborder.

6. The garment of claim 1 further comprising a pair of partially elastic, continuous legborders, and a continuous, elastic legband operatively elastically joined to each said partially elastic, continuous legborder.

7. A disposable garment, comprising:

a pant body comprising a continuous waistborder defining a continuous waist opening, said continuous waistborder comprising at least one non-elastic segment and at least one elastic segment, and a continuous elastic waistband comprising at least one recoverable portion that is capable of being temporarily inhibited, and at least one elastic portion having an elasticity substantially the same as an elasticity of said elastic segment, said continuous elastic waistband being joined to said continuous waistborder with said elastic portion joined to said elastic segment, and said recoverable portion joined to said nonelastic segment, said recoverable portion, upon being activated, gathering said non-elastic segment.

8. The garment of claim 7 wherein said recoverable portion and said non-elastic segment, after being activated, have an elasticity different from the elasticity of said elastic segment.

9. The garment of claim 8 wherein said waistband has a width between about 1 centimeter to about 8 centimeters.

10. The garment of claim 9 wherein said waistband is folded over a peripheral edge of said waistborder.

11. The garment of claim 9 wherein said waistband is C-folded upon itself.

12. The garment of claim 9 wherein said waistband extends beyond a peripheral edge of said waistborder.

13. A disposable absorbent garment, comprising:

a topsheet, a backsheet comprising a waistborder having at least one elastic segment and a non-elastic segment, an absorbent structure disposed on said backsheet, and an elastic waistband joined to said waistborder, and comprising at least one elastic portion and a recoverable portion capable of being temporarily inhibited, said elastic portion being joined to said elastic segment of said waistborder, said recoverable portion being joined to said non-elastic segment of said waistborder, said recoverable portion, upon being activated, gathering said non-elastic segment.

14. The garment of claim 13 wherein said recoverable portion and said non-elastic segment, after being activated, have an elasticity substantially the same as the elasticity of said elastic segment of said waistborder.

15. The garment of claim 13 wherein said recoverable portion and said non-elastic segment, after being activated, have an elasticity different from the elasticity of said elastic segment of said waistborder.

16. The garment of claim 13 wherein said waistband is folded over an edge of said waistborder.

17. The garment of claim 13 wherein said waistband is C-folded upon itself.

18. The garment of claim 13 wherein said waistband extends beyond an edge of said waistborder.

* * * * *